US00PP37194P2

(12) United States Plant Patent
Coetzee

(10) Patent No.: US PP37,194 P2
(45) Date of Patent: Jan. 6, 2026

(54) GRAPEVINE PLANT NAMED 'NAVSEL 70'

(50) Latin Name: *Vitis vinifera*
Varietal Denomination: NAVSEL 70

(71) Applicant: SPECIAL NEW FRUIT LICENSING LIMITED (SNFL), Peterborough (GB)

(72) Inventor: Gideon Jacobus Nicolaas Coetzee, Rawsonville (ZA)

(73) Assignee: SPECIAL NEW FRUIT LICENSING LIMITED (SNFL), Peterborough (GB)

( * ) Notice: Subject to any disclaimer, the term of this patent is extended or adjusted under 35 U.S.C. 154(b) by 0 days.

(21) Appl. No.: 19/219,620

(22) Filed: May 27, 2025

(51) Int. Cl.
*A01H 5/08* (2018.01)
*A01H 6/88* (2018.01)

(52) U.S. Cl.
USPC ..... Plt./205
CPC ..... *A01H 6/88* (2018.05); *A01H 5/08* (2013.01)

(58) Field of Classification Search
USPC ..... Plt./156, 205
See application file for complete search history.

(56) References Cited

U.S. PATENT DOCUMENTS

PP24,551 P3 6/2014 Cain
PP36,520 P2 * 3/2025 Coetzee ..... A01H 6/88 Plt./207

* cited by examiner

*Primary Examiner* — Karen M Redden
(74) *Attorney, Agent, or Firm* — Michael Best & Friedrich LLP

(57) ABSTRACT

'NAVSEL 70' is a new and distinct grapevine plant with novel characteristics that include good fertility and naturally loose bunches. The berries produced by 'NAVSEL 70' are white and seedless with a crunchy and very firm texture and no detectable seed traces. The berries produced by 'NAVSEL 70' are medium, weighing 4.76 g/berry on average, and harvested at the end of August in Murcia, Spain.

1 Drawing Sheet

Latin name of the genus and species: *Vitis vinifera*.
Variety denomination: 'NAVSEL 70'.

BACKGROUND

Described herein is a new and distinct variety of seedless grapevine named 'NAVSEL 70'. The new variety originated from a hybridization performed in Wellington, South Africa in 2008 between 'MUS' (not patented), as the seed parent, and a 'VI-2010-bulk' (not patented), a bulked pollen from several unnamed siblings, as the pollen parent. Abortive seed traces were embryo cultured, and the resulting plant was planted in an evaluation block during 2009. The first evaluation of the fruit produced by 'NAVSEL 70' was performed during 2011. 'NAVSEL 70' was first asexually propagated by field grafting dormant hardwood scions to 1103 Paulsen rootstock (not patented) in 2013 in South Africa. Fruit from the resulting four grafted 'NAVSEL 70' vines was first harvested in 2015. All characteristics and distinctions remain true to form and are established and transmitted through succeeding propagations.

SUMMARY

The following are the most outstanding and distinguishing characteristics of 'NAVSEL 70'. 'NAVSEL 70' produces naturally medium (4.76 g/berry) seedless white (2.5GY7/6) berries. The berries produced by 'NAVSEL 70' have a broad ellipsoid shape with neutral flavor, and very crunchy and firm texture, that are harvested at the end of August in Murcia, Spain.

'NAVSEL 70' is most similar to 'IFG Eleven' (U.S. Plant Pat. No. 24,551). Nonetheless, the new cultivar can be distinguished from 'IFG Eleven' based at least upon berry size, berry texture and berry shape. The berries produced by 'NAVSEL 70' are medium (4.76 g) where the berries produced by 'IFG Eleven' are large (8.9 g). 'NAVSEL 70' has berries with broad ellipsoid shape whilst the berries produced by 'IFG Eleven' has a narrow elliptic shape. The flesh of 'NAVSEL 70' is crisper than the flesh of 'IFG Eleven'.

'NAVSEL 70' can be distinguished from its female parent, 'MUS' (not patented), in that the new cultivar is harvested at the end of August while the harvest time of 'MUS' is in early-July (almost 6 weeks earlier) in Murcia, Spain. The berries produced by 'NAVSEL 70' have a crunchy texture whereas the berries produced by 'MUS' have a juicy texture. The new variety 'NAVSEL 70' produces berries with rudimentary seeds, non-detectable, while the variety 'MUS' produces berries with hard trace.

BRIEF DESCRIPTION OF THE DRAWINGS OR PHOTOGRAPHS

The accompanying-colored photographs illustrate the overall appearance of the 'NAVSEL 70' plant showing the colors as true as it is reasonably possible to obtain in colored reproductions of this type. Colors in the photographs may differ slightly from the color values cited in the detailed botanical description that accurately describe the colors of the plant described herein. These figures are exemplary will vary depending on the plant and distinguishing characteristics.

FIG. 1 shows the form, foliage, and fruit of a 3-year-old 'NAVSEL 70' vine grown in a field in Murcia, Spain. FIG. 1 shows, from the top in a clockwise direction: mature upper surface leaf, immature upper surface leaf, inflorescence, longitudinal section of immature fruits, side view of immature fruits, longitudinal section of mature fruits, side view of mature fruits, a secondary fruit bunch (middle), a cutting of a young shoot with tendrils and leaves, and a primary fruit bunch. The colors shown are as true as can be reasonably obtained by conventional photographic procedures.

DETAILED BOTANICAL DESCRIPTION

The following detailed description sets forth the distinctive characteristics of 'NAVSEL 70'. The detailed botanical description was obtained between March and November using 3-year-old plants grown in fields in Murcia, Spain. The color references are to the Munsell Plant Tissue Color Book, 2012 Edition by Munsell Color.

Classification:

*Family*.—Vitaceae.

*Botanical*.—*Vitis vinifera*.

*Common name*.—Grapevine.

*Cultivar name*.—'NAVSEL 70'.

Plant:

*Plant habit and growth*.—Semi-erect.

*Age at maturity*.—3 years old.

*Size* (*at maturity*).—Height — 225 cm. Width — 300 cm.

*Vigor*.—High.

*Productivity*.—High (1.2 fertility index), around 15 Tn/acre.

*Rootstock*.—Name of rootstock — 1103 Paulsen Rootstock (not patented). Age of rootstock at time of grafting — one year old.

Trunk:

*Size*.—Diameter — 4.4 cm. Height (at measured diameter of 4 cm) — 45 cm above the ground.

*Shape*.—Straight and cylindrical.

*Surface texture*.—Rough, straight grained with the outer layer easily removed.

*Bark color*.—Exterior — 5YR 6/2. Interior — 5YR 4/4.

Canes:

*Size*.—Diameter — 6.40 mm. Length — 126.6 cm.

*Surface texture*.—Mature cane — smooth, slightly grained. Immature cane — very smooth, slightly grained, glabrous.

*Form* (*woody shoot cross section form*).—Circular; pith in center with diaphragm at nodes.

*Color*.—Mature — 5 months, 2.5GY5/8. Immature — 4 weeks, 5GY6/8. Dorsal side of internodes — 2.5GY5/8; anthocyanins — 2.5R5/6. Ventral side of internodes — 2.5GY5/8. Dorsal side of nodes — 2.5GY5/8. Ventral side of nodes — 2.5GY5/8.

*Internode length* (*upper mature sun cane*).—12.4 cm.

*Internode width* (*upper mature sun cane*).—6.3 mm.

*Node width*.—11.2 mm.

Bud:

*Bud description*.—Winter bud — rounded, pointed, color 5YR5/4.Green bud — rounded and pointed, 5GY5/6 without anthocyanins.

*Time of bud burst*.—25 March.

*Time of bud leaf burst*.—2 April.

Tendrils:

*Form*.—Mostly trifid, medium large, smooth, slightly curly.

*Size*.—Length — 26.3 cm. Diameter — 2.10 mm.

*Texture and distribution of tendril at each node beginning at base*.—Smooth, discontinuous, 0000001010001010011001001 00 (0 means no tendril at that node and 1 means there is tendril at the node).

*Color*.—Mature — 4 weeks, 2.5GY6/6. Immature — 10 days, 2.5/8.

*Anthocyanin*.—Mature — not present. Immature — not present.

Growing tips (young shoot):

*Pubescence*.—Absence.

*Color*.—2.5GY5/6.

*Anthocyanin*.—Absent.

*Shape*.—Fully open.

*Apex*.—Triangular.

*Form of tip*.—Fully open.

*Shoot attitude before tying*.—Semi-erect.

Leaves:

*Shape*.—Wedge-shaped.

*Apex*.—Pointed.

*Base*.—Rounded.

*Number of lobes*.—5.

*Depth of upper lateral sinuses of mature leaves*.—Deep.

*Arrangement of lobes of upper lateral sinuses on mature leaves*.—Strongly overlapped.

*Margin*.—Irregular teeth.

*Length of teeth on margin*.—4 to 15 mm.

*Shape of teeth on margin*.—Mixture of both sides straight and both sides convex.

*Texture* (*mature leaf*).—Upper surface — smooth, without goffering or blistering on upper side of blade. Lower surface — smooth, main veins are raised, glabrous

*Size*.—Immature: Length — 10 days, 7.6 cm. Width — 10 days, 7.9 cm. Mature: Length — 4 weeks, 16.25 cm. Width — 4 weeks, 15.1 cm. Ratio of length/width of teeth (mature leaf) — small.

Color:

*Immature leaf*.—Upper surface — 5GY5/6. Lower surface — 2.5GY5/6.

*Mature leaf*.—Upper surface — 5GY5/6. Lower surface — 5GY5/6.

*Autumn coloration*.—Upper surface — 2.5Y7/8. Lower surface — 5Y7/8.

*Venation*.—

*Pattern*.—Palmate (veins on upper leaf are flat; veins on lower leaf are raised), without anthocyanins coloration, glabrous.

*Length of middle vein in mature leaves*.—11.7 cm.

*Color*.—Upper surface — 2.5GY5/6. Lower surface — 5GY7/4, anthocyanins 5R5/4.

*Petiolar sinus*.—Braced-shaped, open, base not limited by veins, wide open.

*Petiole*.—Length — 7.1 cm. Diameter — 2.1 mm.

*Color*.—5GY6/10 (anthocyanins 5R8/4).

Floral cluster:

*General description and location*.—Very large, mostly in the 5th, 100% with shoulders.

*Quantity of inflorescences per cluster*.—4032.

*Size*.—Length — 18.5 cm. Width — 11.4 cm hanging; 21.9 cm with shoulders spread.
*Peduncle*.—Length — 6.3 cm. Diameter — 4.7 mm.
*Inflorescences*.—Hermaphroditic.
*Stamens*.—5 per flower, straight, 2.9 mm.
*Anthers*.—Small, nondescript.
*Date of bloom*.—Start — 29 April, 50% — 5 May, 100% — 13 May.
*Pollen amount*.—Sparse.
*Calyptra*.—5 segments, complete separation.
*Calyptra color*.—5GY6/8.

Fruit:

*Time of year of commercial harvest and shipment*.—19 August in Murcia, Spain.
*Time of beginning of berry ripening*.—Medium season.
*Keeping quality*.—Very good. After 60 days primary and secondary stems are green. The texture of the berries is very firm, without any splits.
*Cluster* (*primary bunches*).—
*General size*.—Medium (531.8 g tipped, 600 g non tipped).
*Length* (*without peduncle*).—20.5 cm non tipped; 30 cm tipped.
*Width*.—14.83 cm hanging, 34.17 cm with shoulders spread.
*Density*.—Medium.
*Peduncle length*.—6.67 cm.
*Peduncle diameter*.—6.2 mm.
*Peduncle color*.—2.5GY 6/6.
*Number of berries per cluster*.—184 (with tipping, on average); 210 (without tipping, on average).
*Berry*.—Size — medium (4.76 g). Diameter — 18.22 mm. Length — 21.73 mm. Shape — broad ellipsoid. Uniformity — very uniform. Brix content — 22.6° Brix. Titratable acidity — 0.52. Skin color (without bloom) — 2.5GY7/6. Skin color (with bloom) — 2.5GY7/6.
*Pedicel*.—Length — 10.82 mm. Diameter — 1.2 mm. Color — 2.5GY8/6. Strength of attachment to berry — strong.

Cluster (secondary bunches):

*General size*.—Small, 146 g.
*Length* (*without peduncle*).—11.125 cm.
*Width*.—8.125 cm hanging; 17.5 cm with shoulders spread.
*Density*.—Lax.
*Peduncle length*.—8 cm.
*Peduncle diameter*.—3.03 mm.
*Peduncle color*.—2.5GY7/8.
*Number of berries per cluster*.—39 (on average).
*Berry*.—Size — medium, 3.1 g. Diameter — 16.22 mm. Length — 18.71 mm. Shape — broad ellipsoid. Uniformity — uniform. Brix content — 18.4° Brix. Titratable acidity — 0.64. Skin color (without bloom) — 2.5GY6/6. Skin color (with bloom) — 2.5GY6/6.
*Pedicel*.—Length — 10.44 mm. Diameter — 1.51 mm. Color — 2.5GY7/6. Strength of attachment to berry — strong.

Berry flesh:

*Color*.—2.5GY8/6.
*Juice, color*.—5Y7/6.
*Juice production*.—High, 39.92%.
*Thickness of skin*.—thin.
*Flavor*.—Neutral.
*Fragrance*.—Neutral.
*Texture*.—Crunchy and very firm (82.3 shores).
*Seeds*.—Seed rudiments, non-detectable.
*Use*.—Table grape.

Disease and insect resistance: This cultivar is susceptible to diseases of its species, such as *Erysiphe necator, Plasmopara viticola, Botrytis cinerea, Daktulosphaira vitifoliae, Ceratitis capitata, Planococcus ficus, Planococcus citri*, and *Empoasca vitis*.

What is claimed is:

1. A new and distinct variety of grapevine plant named 'NAVSEL 70' as substantially described and illustrated herein.

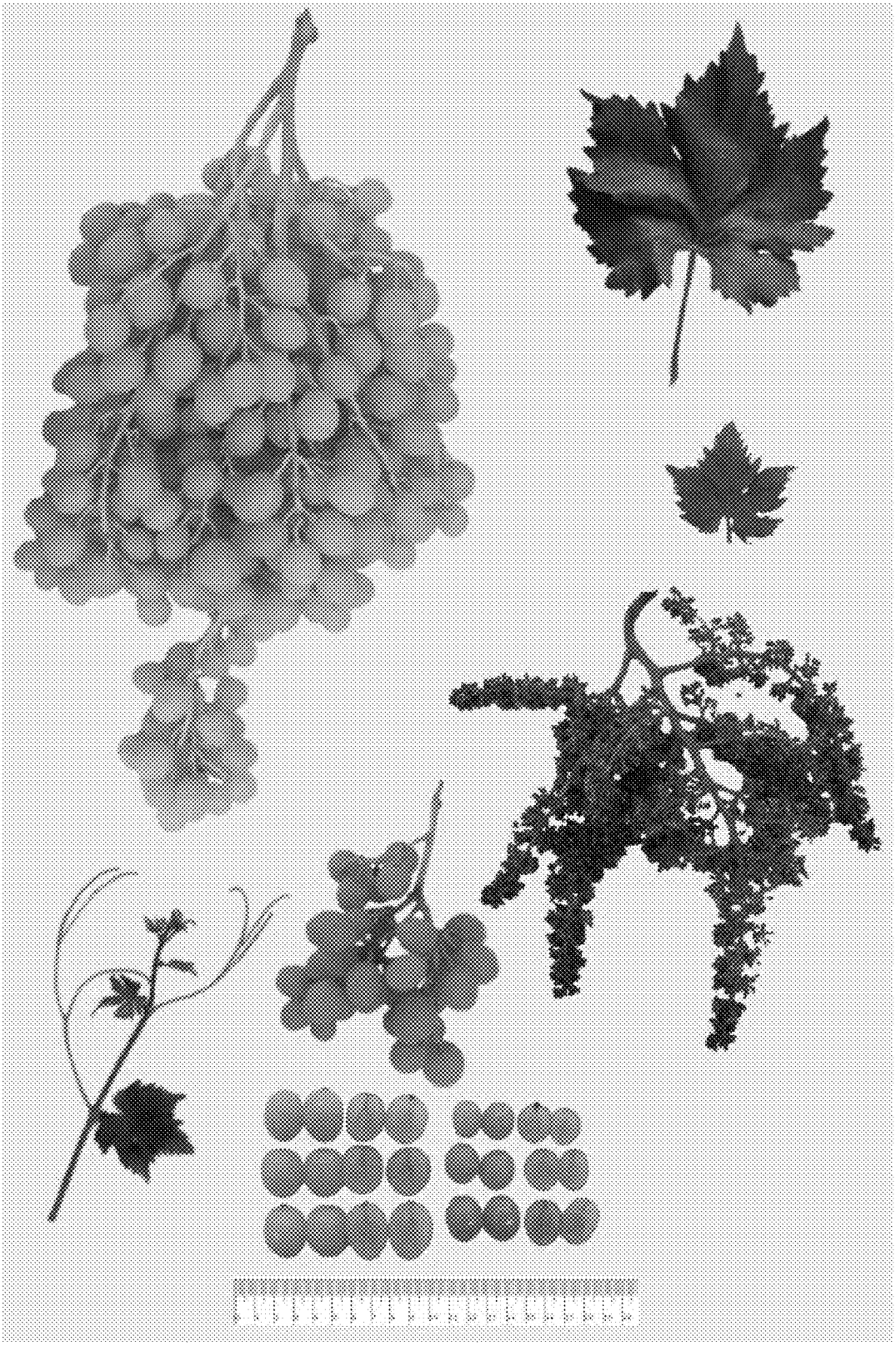

* * * * *